(12) United States Patent
De Stefani et al.

(10) Patent No.: US 11,376,339 B2
(45) Date of Patent: Jul. 5, 2022

(54) AUTOCLAVE STERILISATION PROCESS FOR PRIMARY CONTAINERS MADE OF GLASS

(71) Applicant: NUOVA OMPI S.R.L., Padua (IT)

(72) Inventors: Jimmy De Stefani, Padua (IT); Linda Celeghin, Padua (IT)

(73) Assignee: NUOVA OMPI S.R.L., Padua (IT)

( * ) Notice: Subject to any disclaimer, the term of this patent is extended or adjusted under 35 U.S.C. 154(b) by 0 days.

(21) Appl. No.: 16/311,940

(22) PCT Filed: Aug. 7, 2017

(86) PCT No.: PCT/IB2017/054813
§ 371 (c)(1),
(2) Date: Dec. 20, 2018

(87) PCT Pub. No.: WO2018/029590
PCT Pub. Date: Feb. 15, 2018

(65) Prior Publication Data
US 2019/0209721 A1    Jul. 11, 2019

(30) Foreign Application Priority Data
Aug. 8, 2016  (IT) .................. 102016000083347

(51) Int. Cl.
*A61L 2/07* (2006.01)

(52) U.S. Cl.
CPC ............. *A61L 2/07* (2013.01); *A61L 2202/23* (2013.01)

(58) Field of Classification Search
CPC .. A61L 2/07; A61L 2202/23; A61L 2202/122; A61L 2202/14
See application file for complete search history.

(56) References Cited

U.S. PATENT DOCUMENTS

| | | | | |
|---|---|---|---|---|
| 4,108,601 A | * | 8/1978 | Wolff | A61L 2/24 422/295 |
| 4,203,947 A | * | 5/1980 | Young | A61L 2/07 422/114 |
| 4,759,909 A | * | 7/1988 | Joslyn | A61L 2/07 422/26 |
| 8,784,732 B1 | * | 7/2014 | Lewis | A61L 2/07 422/26 |
| 2006/0200032 A1 | | 9/2006 | Wu | |

FOREIGN PATENT DOCUMENTS

| | | |
|---|---|---|
| DE | 10254446 A1 | 6/2004 |
| DE | 102011088166 A1 | 6/2013 |
| EP | 1452186 A1 | 9/2004 |
| GB | 2541362 A | 2/2017 |
| WO | 0176646 A1 | 10/2001 |
| WO | 2004093936 A2 | 11/2004 |
| WO | 2007099498 A1 | 9/2007 |

* cited by examiner

*Primary Examiner* — Sean E Conley
*Assistant Examiner* — Brendan A Hensel
(74) *Attorney, Agent, or Firm* — Browdy and Neimark, PLLC

(57) ABSTRACT

In the autoclave sterilisation process, the primary glass containers are exposed to a sterilisation treatment with steam pulses.

18 Claims, 3 Drawing Sheets

AUTOCLAVE STERILISATION PROCESS FOR PRIMARY CONTAINERS MADE OF GLASS

The present invention relates to an autoclave sterilisation process for primary containers made of glass, preferably but not necessarily for pharmaceutical use.

To date, the most widely used sterilisation process of primary glass containers for pharmaceutical use consists of a sterilisation treatment with steam, such as saturated and/or superheated to a predetermined constant temperature which extends continuously for a predetermined exposure time. Typically in the pharmaceutical sector, reference is made to a minimum exposure time named F0 of 15 minutes at a constant temperature of 121.11° C. (250° F.), calculated for an ideal microorganism having a temperature coefficient of destruction (Z) equal to 10.

The sterilisation process with steam is very simple and extremely cost-effective in terms of decontamination.

However, the onset of some defects was observed, especially in glass phials for pharmaceutical use thus treated, consisting essentially in the formation of white patches typically at the shoulder of the phials.

The technical task of the present invention is to solve the drawbacks of the prior art related to the steam sterilisation process of primary containers made of glass, in particular for pharmaceutical use.

As part of this technical task, an object of the invention is to provide an autoclave sterilisation process of primary containers made of glass which is simple and effective, capable of eliminating the occurrence of defects in the primary glass containers treated while maintaining the sterility thereof.

The technical task, as well as this and other objects of the present invention, are achieved by an autoclave sterilisation process for primary containers made of glass, characterised in that the primary containers are exposed in autoclave to a sterilisation treatment with a pulsed flow of steam sequentially fed into the autoclave.

The autoclave therefore operates by controlling the flow of steam based on parameters indicative of operating conditions of the treatment chamber of the autoclave.

The pulsed cycle allows achieving the equivalent exposure time required by pharmaceutical companies by limiting the chemical and physical interaction between the steam and the glass of the primary glass containers.

These and other aspects of the invention will be better clarified by the following description of a preferred embodiment of the sterilisation process, shown by way of a non-limiting example with reference to the accompanying drawings, in which.

Figure 1:
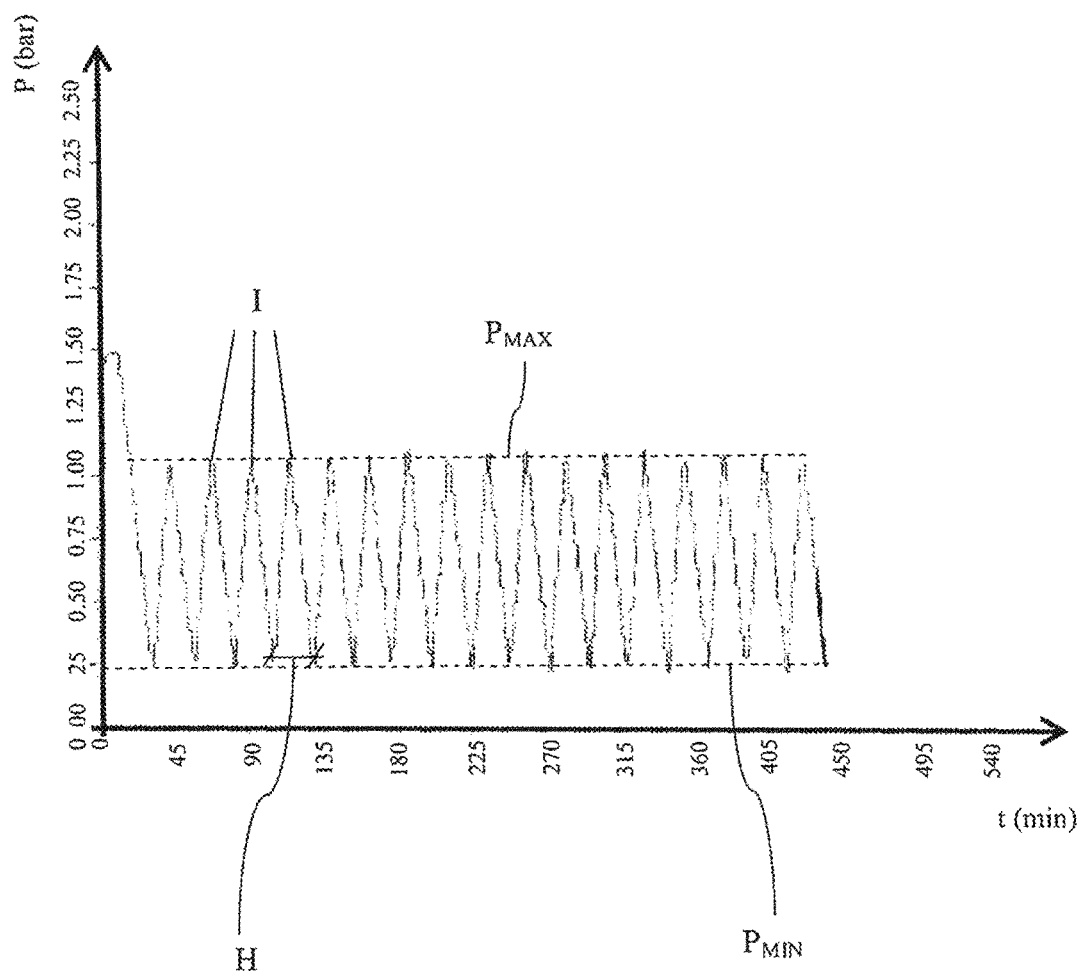
FIG. 1 shows an example of the pressure pattern in the treatment chamber of the autoclave during the sterilisation treatment according to the invention.

The process for killing microorganisms with steam is defined by some important parameters.

D is defined as the time (in minutes) required to reduce to one tenth, at a well-defined temperature, the initial number of microorganisms.

For typical microorganisms (e.g. *Clostridium botlinum, Bacillus subtilis, Bacillus megaterium, Clostridium sporogenes*), the values of D, at a temperature equal to 121.11° C. (250° F.), are typically less than 2 minutes.

Z is the microbiological destruction temperature coefficient defined as the temperature rise (expressed in ° C.) to be made to reduce to one tenth the value D.

For typical microorganisms (e.g. *Clostridium botlinum, Bacillus subtilis, Bacillus megaterium, Clostridium sporogenes*), the values of Z generally range between 6 and 13.

Finally, F0 is the equivalent exposure time at 121.11° C. calculated for an ideal microorganism having a temperature coefficient of destruction Z equal to 10.

For F0, the following formula applies:

$$F0 = \int_0^t 10^{(T0-121.11)/10} dt \qquad (1)$$

Where t is time and T is the actual exposure temperature, as a function of time t.

F0 therefore represents the value of the area under the curve $10^{(T-121.11)/10}$ between time t=0 and time t that represents the duration of the sterilisation treatment.

The autoclave sterilisation process for primary containers 8 made of glass for pharmaceutical use provides that the primary containers 8 are placed in an autoclave and are exposed to a sterilisation treatment with a pulsed flow F of steam, such as saturated and/or superheated, controlled on the basis of a parameter indicative of operating conditions of the treatment chamber 10 of the autoclave, such as pressure, temperature and/or other parameters.

In practice, the autoclave has a constant volume treatment chamber 10 provided with an inlet way 12 connected to a steam generator 14 and an outlet way 16 of the steam.

The saturated steam generator 14 further has a supply pump 18 of the treatment chamber 10.

Both the inlet way 12 and the outlet way 16 of the treatment chamber 10 are provided with a respective shut-off valve 20.

In a preferred embodiment, in which the process control takes place on the basis of the steam pressure in the treatment chamber 10, the sterilisation process is carried out as follows.

In the starting configuration of the autoclave, the shut-off valve 20" of the outlet way 16 of the treatment chamber 10 is closed and the shut-off valve 20' of the inlet way 12 of the treatment chamber 10 is open.

The steam generator 14 generates steam, for example at 100° C. and 1 Atm, and feeds a first pulse of steam in the treatment chamber 10 through the supply pump 18.

The supply pump 18 remains activated, subjecting the steam in the treatment chamber 10 to an increasing pressure ramp until the steam pressure P into the treatment chamber 10 reaches a preset maximum pressure value Pmax.

When pressure Pmax is reached, the controller simultaneously controls the closing of the shut-off valve 20' of the inlet way 12 of the treatment chamber 10, the opening of the shut-off valve 20" of the outlet way 16 from which the first pulse of the steam flow outflows, and the reversal of the supply pump 18 which aids the discharge from the treatment chamber 10 of the first pulse of the steam flow.

The supply pump 18 remains activated in reverse operation, subjecting the residual steam in the treatment chamber 10 to a decreasing pressure ramp until the steam pressure P into the treatment chamber 10 reaches a preset minimum pressure value Pmin.

When pressure Pmin is reached, the controller simultaneously controls the closing of the shut-off valve 20" of the outlet or discharge way 16 of the treatment chamber 10, the opening of the shut-off valve 20' of the inlet way 12 of the treatment chamber 10, the activation of the supply pump 18 in direct operation, and the executing of a same cycle for the second pulse of steam flow, and so on until the last programmed pulse of the steam flow.

It should be noted that, in this way, the mass of steam that is sent in the form of pulses in the treatment chamber 10 and therefore to containers 8 to be treated varies continuously: in other words, the steam mass system of the treatment chamber 10 is an open system whereby each pulse (and thus the respective mass of steam) is first introduced into the treatment chamber 10 and then discharged from the same treatment chamber 10. The fact that the mass of steam that acts on the primary containers 8 is not constant but changes over time involves the technical advantage of reducing the impact of steam on glass, thus preserving the container from damage and maintaining the same degree of sterility. The primary containers 8 are exposed to the sterilisation treatment up to achieving an exposure time calculated on the basis of F0.

In particular, the value of the exposure time is such that the equivalent value of F0 at a constant temperature of 121.11° C., calculated for an ideal microorganism with a temperature coefficient of destruction Z equal to 10 is not less than a value indicative of the successful sterilisation, such as 15 minutes.

Figure 2:
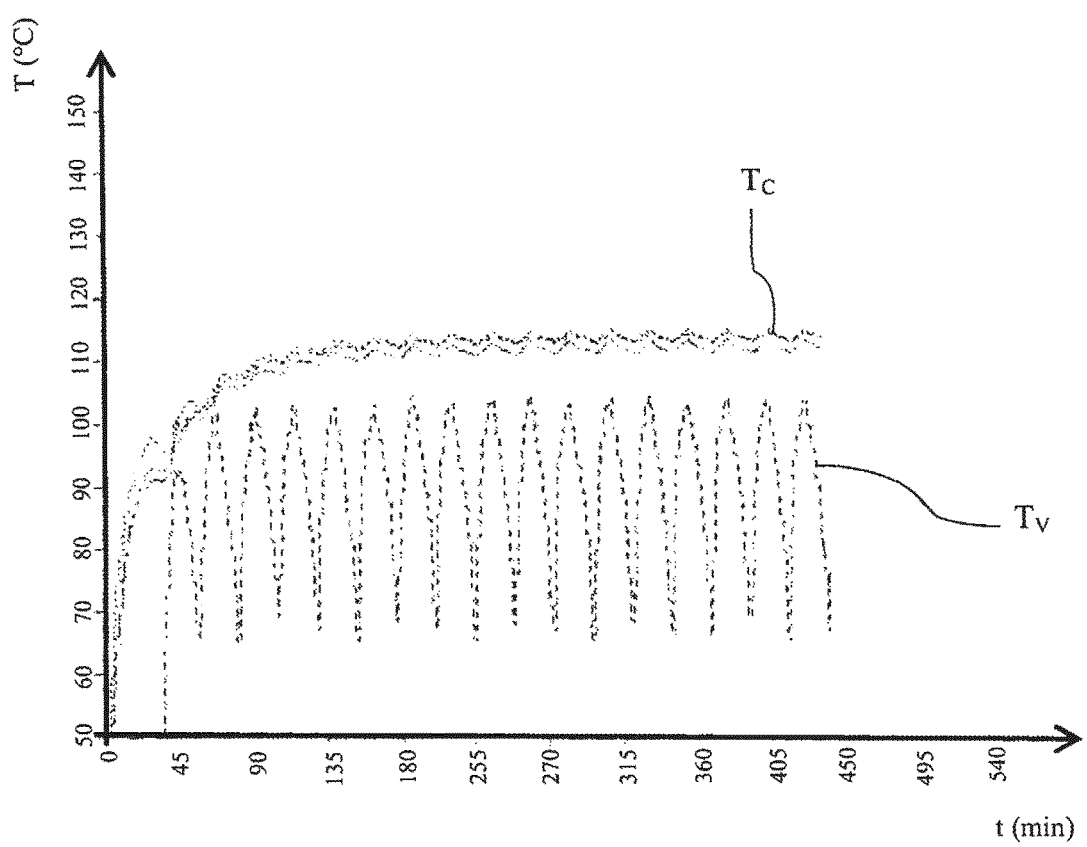
FIG. 2 shows the corresponding pattern of temperature Tv of steam in the treatment chamber and temperature Tc of the primary glass containers.
Figure 3:
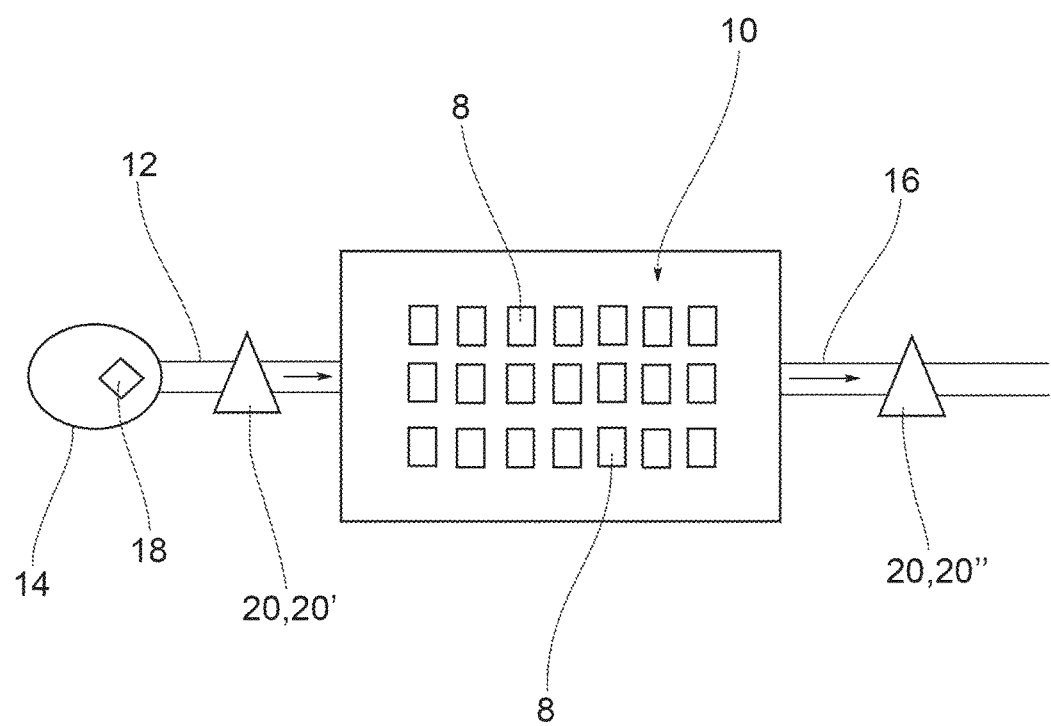
FIG. 3 shows an exemplary diagram of a sterilisation plant of primary containers according to an embodiment of the present invention.

As shown in FIG. 2, therefore, also the temperature has a pulsed pattern.

Preferably, the threshold values of pressure P (Pmin and Pmax) of steam in the treatment chamber 10 of all pulses Φ of the flow, comprised within a cycle, are identical.

In particular, for the proposed sterilisation of primary containers 8 made of glass for pharmaceutical use, it has been found to be convenient to select a maximum value Pmax if pressure P equal to 1.10±0.05 bar and a minimum value Pmin of pressure P equal to 0.25±0.05 bar.

In particular, for the proposed sterilisation, it has been found to be convenient to adopt a constant amplitude H of the pressure pulse for all the pulses of the flow, such an amplitude value H is equal to 24 min.±1.5 min. Amplitude therefore means the duration of each pulse, represented in the figures on the abscissa axis.

This means that for the proposed sterilisation, the treatment chamber 10 empties completely upon switching from one steam pulse to the next.

In a further embodiment, the threshold values (min and max) of pressure P and/or another parameter indicative of operating conditions of the process, comprised within a cycle, may differ.

The flow and pressure pulse shape may be also different from the one described and illustrated and can be modulated experimentally to optimise the results in terms of reduction or complete elimination of the number of defective products. In practice, the specific pattern of the flow pulses and parameters indicative of operating process conditions used to achieve the desired value of F0 is unimportant.

What matters is the fact that the sterilisation treatment is no longer carried out by uninterruptedly exposing the primary containers 8 made of glass to a constant temperature of steam, but by exposing them to a pulsed flow of steam having parameters indicative of operating process conditions that are in turn pulsed. In other words, both temperature and pressure are pulsed. It should be noted, therefore, that there are no sterilisation steps in which pressure and/or temperature reach static sterilisation steps (such as the classic plateau of about 121 C used in the prior art), i.e. are kept constant, but rather these pressure and temperature parameters in the treatment chamber 10 continue to vary within predetermined limits (minimum and maximum) throughout the sterilisation step of the primary containers 8.

In this way, it is possible to inhibit the initiation of processes that create defects in the primary glass containers 8, particularly in relation to the formation of white patches and potential damage to the physical and chemical structure of the glass.

Therefore, the treatment chamber 10 is an open system, in which the method provides for introducing new mass of steam when the pressure in said treatment chamber reaches a predetermined minimum value Pmin and the step of ejecting from the treatment chamber 10 a mass of steam previously introduced when the pressure reaches a predetermined maximum value Pmax. The fact that the treatment chamber 10 is an open mass system ensures the progressive replacement of the mass of steam, thus preserving the container from damage while maintaining at the same time, the same degree of sterility for an optimal sterilisation process.

The method, as seen, involves the steps of continuously changing the pressure and/or temperature parameters of steam inside the treatment chamber 10 throughout the sterilisation step. This constant changing of the pressure and temperature parameter, also related to the continuous replacement of the mass of steam contributes to improving the efficiency of the sterilisation process in the treatment chamber 10.

In fact, it has been verified that the provision of continuously adding and subtracting different masses of steam inside the treatment chamber 10 throughout the sterilisation step improves the sterilisation itself compared to the prior art solutions with constant mass.

Several changes and variations may be made to the sterilisation process thus conceived, all falling within the protection scope of the invention.

For example, both temperature and pressure pulses may not be constant in amplitude, but have absolute values different from each other. Moreover, the duration of the same pulses may vary: in other words, the temporal duration of both temperature and pressure pulses may not be constant over time, but variable.

In one embodiment, for example, containers 8, such as phials, ampoules, cartridges, syringe cylinders etc., are housed inside a secondary container comprising a bottom and side walls that define a containment compartment, and a secondary container inlet mouth, and a removable lid applicable to close the inlet mouth, wherein the secondary container is steam-permeable.

In a further embodiment, the glass containers are used in a scope other than the pharmaceutical industry.

The invention claimed is:

1. An autoclave sterilization process for primary containers made of glass, comprising:
   exposing said primary containers, in a treatment chamber of an autoclave, to a sterilization treatment with a pulsed flow of steam sequentially fed into the treatment chamber, and
   controlling the pulsed flow of steam on the basis of at least one parameter indicative of operating conditions of the autoclave,
   wherein said parameter indicative of operating conditions of the autoclave is the pressure of the steam in the treatment chamber,
   wherein the sterilization treatment comprises introducing a new mass of steam when the pressure in the treatment chamber reaches a predetermined minimum value and ejecting from the treatment chamber a mass of steam previously introduced when the pressure reaches a predetermined maximum value, and wherein the ejecting of the mass of steam comprises closing a shut-off valve disposed in an inlet of the treatment chamber, opening of a shut-off valve disposed in an outlet of the treatment chamber to cause the first pulse of the steam to flow out of the treatment chamber, and reversing operation of a steam supply pump, wherein said pressure displays a pulsed pattern.

2. The autoclave steam sterilization process for primary containers made of glass according to claim 1, wherein said primary containers are treated for a time of exposure to said flow such that the value of the equivalent time of exposure at a constant temperature of 121.11° C., calculated for an ideal microorganism having a temperature coefficient of destruction of 10, is not less than a value indicating that sterilization has taken place.

3. The autoclave steam sterilization process for primary containers made of glass according to claim 1, wherein the pressure pulses in said treatment chamber all have the same maximum value.

4. The autoclave steam sterilization process for primary containers made of glass according to claim 1, wherein the pressure pulses in said treatment chamber have a maximum pressure value equal to 1.10±0.05 bar.

5. The autoclave steam sterilization process for primary containers made of glass according to claim 1, wherein the pressure pulses in said treatment chamber all have the same minimum value.

6. The autoclave steam sterilization process for primary containers made of glass according to claim 1, wherein the pressure pulses in said treatment chamber have a minimum pressure value equal to 0.25±0.05 bar.

7. The autoclave steam sterilization process for primary containers made of glass according to claim 1, wherein the pressure pulses in said treatment chamber all have the same duration.

8. The autoclave steam sterilization process for primary containers made of glass according to claim 1, wherein each of the pressure pulses in said treatment chamber have duration equal to 24±1.5 minutes.

9. The autoclave steam sterilization process for primary containers made of glass according to claim 1, wherein the pulses of the flow of steam are all identical.

10. The autoclave steam sterilization process for primary containers made of glass according to claim 1, wherein said pressure pulses are all identical.

11. The autoclave steam sterilization process for primary containers made of glass according to claim 1, wherein a programmed number of pulses of the flow of steam follow one another, without any interruption between the preceding and subsequent pulse of the flow.

12. The autoclave steam sterilization process for primary containers made of glass according to claim 1, wherein the containers are of a pharmaceutical type selected from bottles, phials, cartridges, and syringe cylinders.

13. The autoclave steam sterilization process for primary containers made of glass according to claim 1, wherein the steam is saturated and/or superheated.

14. The autoclave steam sterilization process for primary containers made of glass according to claim 1, wherein the method further comprises continuously changing pressure and/or temperature parameters of the steam inside the treatment chamber during the sterilization treatment.

15. The autoclave steam sterilization process for primary containers made of glass according to claim 1, wherein the method further comprises continuously adding and subtracting different masses of steam inside the treatment chamber during the sterilization treatment.

16. The autoclave steam sterilization process for primary containers made of glass according to claim 1, wherein the step of exposing comprises:

generating steam at a predetermined temperature and pressure;

feeding a first pulse of the steam into the treatment chamber through a supply pump;

operating the supply pump to continue to supply steam into the treatment chamber in an increasing pressure ramp until the pressure of the steam into the treatment chamber reaches a preset maximum pressure value;

when the preset maximum pressure value is reached, simultaneously controlling, via a controller, closing of the shut-off valve disposed in the inlet of the treatment chamber, opening of the shut-off valve disposed in the outlet of the treatment chamber to cause the first pulse of the steam to flow out of the treatment chamber, and reversing operation of the supply pump;

controlling the supply pump to remain in the reverse operation subjecting any residual steam in the treatment chamber to a decreasing pressure ramp until the pressure of the steam in the treatment chamber reaches a preset minimum pressure value;

when the preset minimum pressure value is reached, simultaneously controlling, via the controller, closing of the shut-off valve disposed in the outlet, opening of the shut-off valve disposed in the inlet, and reversing operation of the supply pump again to pump steam into the treatment chamber through the inlet to feed a second pulse of steam flow into the treatment chamber; and repeating the step of exposing for a predetermined time period, wherein the treatment chamber is completely emptied upon switching from one steam pulse to the next.

17. The autoclave steam sterilization process for primary containers made of glass according to claim 1, wherein the step of exposing comprises:

generating steam at a predetermined temperature and pressure;

feeding a first pulse of the steam into the treatment chamber through a supply Pump;

operating the supply pump to continue to supply steam into the treatment chamber in an increasing pressure ramp until the pressure of the steam into the treatment chamber reaches a preset maximum pressure value;

when the preset maximum pressure value is reached, simultaneously controlling, via a controller, closing of the shut-off valve disposed in the inlet of the treatment chamber, opening of the shut-off valve disposed in the outlet of the treatment chamber to cause the first pulse of the steam to flow out of the treatment chamber, and reversing operation of the supply pump;

controlling the supply pump to remain in the reverse operation subjecting any residual steam in the treatment chamber to a decreasing pressure ramp until the pressure of the steam in the treatment chamber reaches a preset minimum pressure value;

when the preset minimum pressure value is reached, simultaneously controlling, via the controller, closing of the shut-off valve disposed in the outlet, opening of the shut-off valve disposed in the inlet, and reversing operation of the supply pump again to pump steam into the treatment chamber through the inlet to feed a second pulse of steam flow into the treatment chamber; and repeating the step of exposing for a predetermined time period.

18. The autoclave steam sterilization process for primary containers made of glass according to claim 1, wherein the preset maximum pressure value is equal to 1.10±0.05 bar and the preset minimum pressure value is equal to 0.25±0.05 bar.

* * * * *